US00PP32153P2

(12) United States Plant Patent
Lewis

(10) Patent No.: US PP32,153 P2
(45) Date of Patent: Sep. 1, 2020

(54) ***CROCOSMIA* PLANT NAMED 'FIRE STARTER'**

(50) Latin Name: ***Crocosmia* X *hybrida***
Varietal Denomination: Fire Starter

(71) Applicant: Paul Lewis, Newport (GB)

(72) Inventor: Paul Lewis, Newport (GB)

( * ) Notice: Subject to any disclaimer, the term of this patent is extended or adjusted under 35 U.S.C. 154(b) by 0 days.

(21) Appl. No.: 16/602,210

(22) Filed: Aug. 28, 2019

(51) Int. Cl.
*A01H 5/02* (2018.01)

(52) U.S. Cl.
USPC ..... Plt./419

(58) Field of Classification Search
USPC ..... Plt./419
CPC ..... A01H 5/02; A01H 6/00
See application file for complete search history.

*Primary Examiner* — Keith O. Robinson
(74) *Attorney, Agent, or Firm* — C. A. Whealy

(57) ABSTRACT

A new and distinct cultivar of *Crocosmia* plant named 'Fire Starter', characterized by its upright plant habit; strong, sturdy and resistance to lodging; moderately vigorous to vigorous growth habit; freely flowering habit; numerous and relatively large and upward-facing yellow, yellow orange and orange red-colored flowers; and good garden performance and winter hardiness.

2 Drawing Sheets

Botanical designation: *Crocosmia* X *hybrida*.
Cultivar denomination: 'FIRE STARTER'.

BACKGROUND OF THE INVENTION

The present invention relates to a new and distinct cultivar of *Crocosmia* plant, also referred to as *Montbretia*, botanically known as *Crocosmia* X *hybrida* and hereinafter referred to by the name 'Fire Starter'.

The new *Crocosmia* plant is a product of a planned breeding program conducted by the Inventor in Carisbrook, Newport, The Isle of Wight, United Kingdom. The objective of the breeding program is to create new upright and strong *Crocosmia* plants with large attractive upward-facing flowers, a long flowering period and winter hardiness.

The new *Crocosmia* plant originated from a cross-pollination made by the Inventor in Carisbrook, Newport, The Isle of Wight, United Kingdom on Jul. 10, 2007 of two unnamed seedling selections of *Crocosmia* X *hybrida*, not patented. The new *Crocosmia* plant was discovered and selected by the Inventor as a single flowering plant from within the progeny of the stated cross-pollination in a controlled greenhouse environment in Carisbrook, Newport, The Isle of Wight, United Kingdom on Aug. 14, 2009.

Asexual reproduction of the new *Crocosmia* plant by divisions in a controlled greenhouse environment in Carisbrook, Newport, The Isle of Wight, United Kingdom since the spring of 2010 has shown that the unique features of this new *Crocosmia* plant are stable and reproduced true to type in successive generations.

SUMMARY OF THE INVENTION

Plants of the new *Crocosmia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Fire Starter'. These characteristics in combination distinguish 'Fire Starter' as a new and distinct *Crocosmia* plant:

1. Upright plant habit; strong, sturdy and resistance to lodging.
2. Moderately vigorous to vigorous growth habit.
3. Freely flowering habit.
4. Numerous and relatively large and upward-facing yellow, yellow-orange and orange red-colored flowers.
5. Good garden performance and winter hardiness.

Plants of the new *Crocosmia* differ primarily from plants of the parent selections in the following characteristics:

1. Plants of the new *Crocosmia* are more freely flowering than plants of the parent selections.
2. Plants of the new *Crocosmia* have larger flowers than plants of the parent selections.
3. Plants of the new *Crocosmia* are more winter hardy than plants of the parent selections.

Plants of the new *Crocosmia* can be compared to plants of *Crocosmia* X *crocosmiiflora* 'Babylon', not patented. In side-by-side comparisons, plants of the. new *Crocosmia* differ primarily from plants of 'Babylon' in flower color as plants of the new *Crocosmia* have yellow, yellow orange and orange red-colored flowers whereas plants of 'Babylon' have orange red-colored flowers.

BRIEF DESCRIPTION OF THE PHOTOGRAPHS

The accompanying colored photographs illustrate the overall appearance of the new *Crocosmia* plant showing the colors as true as it is reasonably possible to obtain in colored reproductions of this type. Colors in the photographs may differ slightly from the color values cited in the detailed botanical description which accurately describe the colors of the new *Crocosmia* plant.

The photograph on the first sheet comprises a side perspective view of typical flowering plants of 'Fire Starter' grown in an outdoor nursery.

The photograph on the second sheet is a close-up view of typical inflorescences of 'Fire Starter'.

DETAILED BOTANICAL DESCRIPTION

The aforementioned photographs and following observations and measurements describe plants of the new *Crocosmia* grown during the summer in an outdoor nursery in Hillegom, The Netherlands. During the production of the plants, day temperatures ranged from 16° C. to 30° C. and night temperatures ranged from 8° C. to 20° C. Plants were one year old when the photographs and the description were taken. In the following description, color references are made to The Royal Horticultural Society Colour Chart, 2015 Edition, except where general terms of ordinary dictionary significance are used.

Botanical classification: *Crocosmia* X *hybrida* 'Fire Starter'.

Parentage:

*Female, or seed, parent*.—Unnamed seedling selection of *Crocosmia* X *hybrida*, not patented.

*Male or pollen parent*.—Unnamed seedling selection of *Crocosmia* X *hybrida*, not patented.

Propagation:

*Type*.—By in vitro meristem culture.

*Time to initiate roots*.—About one week at temperatures about 20° C.

*Time to produce a rooted young plant*.—About seven weeks at temperatures ranging from 15° to 20° C.

*Root description*.—Medium in thickness, fleshy and fibrous; brown in color, actual color of the roots is dependent on substrate composition, water quality, fertilizer type and formulation, substrate temperature and physiological age of roots.

*Rooting habit*.—Low branching; medium density.

*Corms*.—To date, corm development has not been observed on plants of the new *Crocosmia*.

Overall plant description:

*Plant and growth habit*.—Upright plant habit; overall plant shape, narrowly oblong with slightly arching flowering stems; moderately vigorous to vigorous growth habit; strong stems that develop at the plant base and resist lodging; moderate to rapid growth rate.

*Plant height, soil level to top of foliar plane*.—About 105 cm.

*Plant height, soil level to top of floral plane*.—About 108 cm.

*Plant diameter* (*spread*).—About 24.3 cm.

Stem description:

*Aspect*.—Mostly upright.

*Length*.—About 66.6 cm.

*Diameter*.—About 5.5 mm.

*Internode length*.—About 19 cm.

*Strength*.—Strong.

*Texture and luster*.—Smooth, glabrous, waxy; slightly glossy.

*Color, when developing*.—Close to 146D tinged with close to N199A.

*Color, developed*.—Close to 200C; under surface tinged with close to 146B; waxy cuticle, close to 198B to 198C.

Leaf description:

*Appearance*.—Simple, distichous; sessile.

*Quantity per stem*.—About seven.

*Length*.—About 54.9 cm.

*Width*.—About 2.8 cm.

*Shape*.—Ensiform, moderately plicate.

*Apex*.—Narrowly acuminate.

*Base*.—Sheathing; sheath is about 36.8 cm in length, 9 mm in width and close to 143B in color.

*Margin*.—Entire.

*Texture and luster, upper and lower surfaces*.—Smooth, glabrous; matte.

*Venation pattern*.—Camptodrome.

*Color*.—Developing leaves, upper and lower surfaces: Close to 137A. Fully expanded leaves, upper and lower surfaces: Close to 137A and 137B; venation, close to 138A.

Flower description:

*Flower type and habit*.—Single tubular flowers arranged on terminal rhipidiums; flowers sessile; flowers face mostly outwardly and upward-facing; perianth segments fused; freely flowering habit with about 75 flowers developing per inflorescence.

*Natural flowering season*.—Flowering continuous in July and August in The Netherlands; plants begin flowering about six months after planting.

*Fragrance*.—None detected.

*Flower longevity on the plant*.—About ten days; flowers not persistent.

*Flower buds*.—Length: About 2.6 cm. Diameter: About 6 mm. Shape: Narrowly obovate, slightly curved downward. Texture and luster: Smooth, glabrous, moderately velvety; matte. Color: Close to 34A; towards the mid-section, close to between N34A and 185A; towards the base, close to 153B to 153C; immature sepals, upper surface, close to 187A; immature sepals, lower surface, close to 187A slightly tinged with close to 147D.

*Inflorescence length*.—About 31 cm.

*Inflorescence diameter*.—About 20.2 cm.

*Flower diameter*.—About 4.1 cm by 4.4 cm.

*Flower length*.—About 4.9 cm.

*Flower throat diameter*.—About 7 mm.

*Flower tube length*.—About 2.5 cm.

*Flower tube diameter*.—About 7.5 mm to 9 mm.

*Perianth*.—Arrangement: Six arranged in two whorls, each whorl with three segments fused towards the base; inner whorl of perianth segments has a larger dorsal segment and two smaller lateral segments that are similar to outer whorl segments. Inner perianth dorsal segment: Length: About 4.9 cm. Width: About 1 cm. Shape: Obovate; proximally, 55% of the length of the segment is fused into a tube. Apex: Narrowly obtuse to broadly and bluntly acute. Margin: Entire. Texture and luster, upper and lower surfaces: Smooth, glabrous, moderately velvety; matte. Color, when opening, upper surface: Close to 14A; towards the apex, margins and central band, close to N30A. Color, when opening, lower surface: Close to 17B; towards the margins, close to N30A. Color, fully opening, upper surface: Close to 13A; towards the apex and margins, close to N30A; central band, close to N30B; venation, close to 25A and towards the margins, close to N30A; color does not change with development. Color, fully opening, lower surface: Close to 13A; towards the apex and margins, close to N30A; central band, close to N30B; venation, close to 25A; color does not change with development. Inner perianth lateral segments and outer perianth segments: Length: About 4.4 cm. Width, inner lateral segments: About 9 mm. Width, outer segments: About 7 mm. Shape: Obovate; proximally, 55% of the length of the segment is fused into a tube. Apex: Narrowly obtuse to broadly and bluntly acute. Margin: Entire. Texture and luster, upper and lower surfaces: Smooth, glabrous, moderately velvety; matte. Color, when opening, upper surface: Close to 14A; towards the apex, margins and central band, close to N30A. Color, when opening, lower surface: Close to 17B; towards the margins, close to N30A. Color, fully opening, upper surface: Close to 14A; towards the apex and margins, close to N30B; central band, close to N30A; venation, close to 25A and towards the margins, close to N30A; color does not change with development. Color, fully opening, lower surface: Close to 14A; towards the apex and margins, close to N30B; central band, close to N30A; venation, close to 25A; color does not change with development. Flower throat and tube: Texture and luster: Smooth, glabrous, moderately velvety; matte. Color, throat: Close to 42A; venation, close to 42A. Color, tube: Close to 42B; venation, close to 42B.

*Sepals*.—Arrangement: Three in a single whorl. Length: About 8 mm. Width: About 4 mm. Shape: Broadly oblong. Apex: Praemorse. Base: Broadly cuneate, fused. Margin: Entire. Texture and luster, upper surface: Smooth, glabrous; slightly glossy. Texture and luster, lower surface: Smooth, glabrous; matte. Color, when opening, upper and lower surfaces: Close to 178A; towards the base, close to 146B. Color, fully opened, upper and lower surfaces: Close to 178A; towards the base, close to 146B.

*Peduncles*.—Length: About 30.2 cm. Diameter: About 3.5 mm. Strength: Strong. Angle, primary peduncles: Proximally, erect; distally, arching to about 80° from vertical. Angle, lateral peduncles: About 45° from primary peduncle axis. Texture: Smooth, glabrous, waxy; matte. Color, upper surface: Close to 200B; waxy cuticle, close to 198B to 198C. Color, lower surface: Close to 148A; waxy cuticle, close to 198B to 198C.

*Reproductive organs*.—Stamens: Quantity per flower: Typically three. Filament length: About 2.5 cm. Filament color: Close to 14A to 14B. Anther shape: Narrowly sagittate. Anther size: About 9 mm by 1.25 mm. Anther color: Close to 22A. Pollen amount: Scarce. Pollen color: Close to 15D. Pistils: Quantity per flower: One. Pistil length: About 4.4 cm. Style length: About 3.9 cm. Style color: Close to 15A; distally, close to 30A. Stigma shape: Three-parted, curved. Stigma size: About 5 mm by 6 mm. Stigma color: Close to 20A. Ovary color: Close to 144A.

*Fruits and seeds*.—To date, fruit and seed development have not been observed on plants of the new *Crocosmia*.

Pathogen & pest resistance: To date, plants of the new *Crocosmia* have not been observed to be resistant to pathogens and pests common to *Crocosmia* plants.

Garden performance: Plants of the new *Crocosmia* have been observed to have good garden performance, to resist lodging and to tolerate wind, rain and temperatures ranging from about −17° C. to about 35° C.; plants of the new *Crocosmia* are suitable for USDA Hardiness Zones 6 to 10.

It is claimed:

1. A new and distinct *Crocosmia* plant named 'Fire Starter' as illustrated and described.

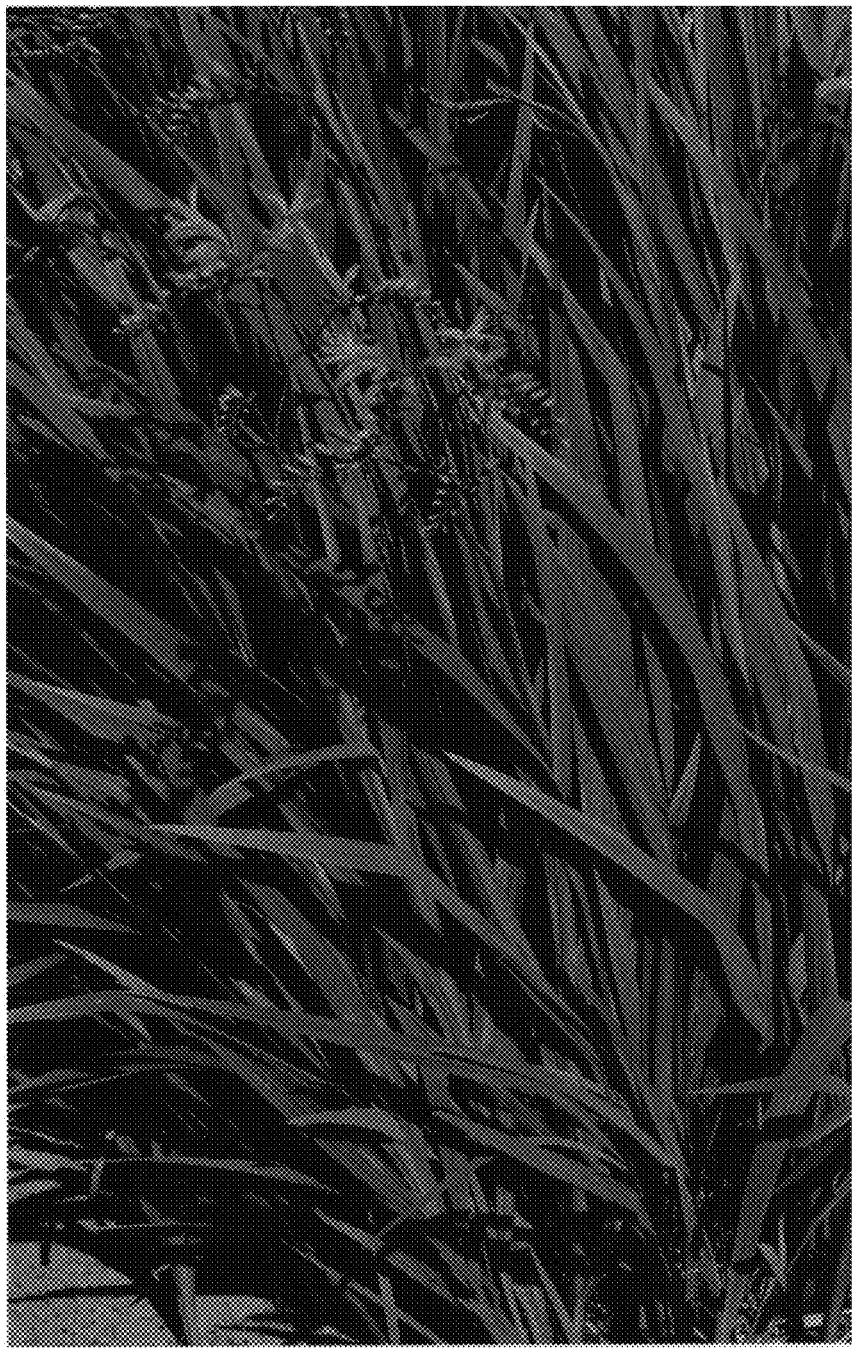

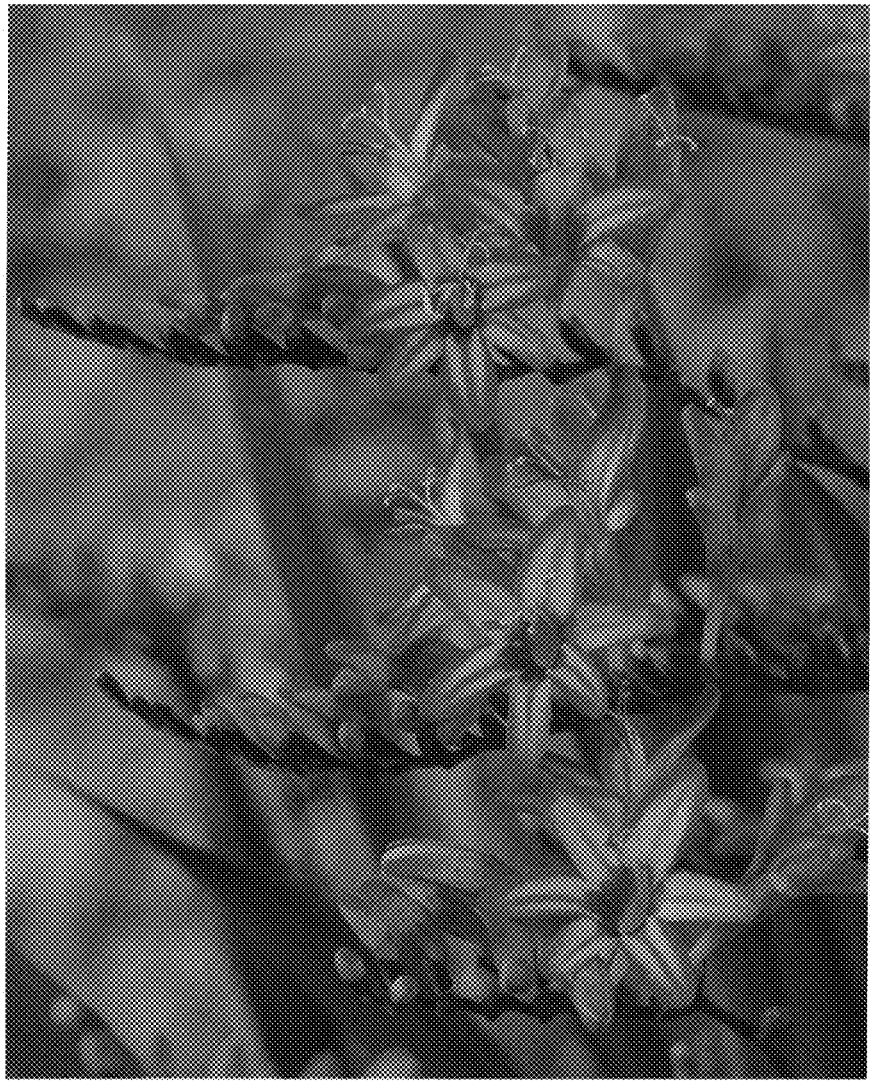

* * * * *